US012026318B2

(12) United States Patent
Wei

(10) Patent No.: US 12,026,318 B2
(45) Date of Patent: Jul. 2, 2024

(54) METHOD AND APPARATUS FOR DETERMINING PRESSURE REFERENCE VALUE, AND CHIP AND ELECTRONIC DEVICE

(71) Applicant: SHENZHEN GOODIX TECHNOLOGY CO., LTD., Shenzhen (CN)

(72) Inventor: Haijun Wei, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 407 days.

(21) Appl. No.: 17/495,501

(22) Filed: Oct. 6, 2021

(65) Prior Publication Data

US 2022/0253145 A1 Aug. 11, 2022

Related U.S. Application Data

(63) Continuation of application No. PCT/CN2021/075406, filed on Feb. 5, 2021.

(51) Int. Cl.
*G06F 3/01* (2006.01)
*G01L 5/00* (2006.01)

(52) U.S. Cl.
CPC ................ *G06F 3/017* (2013.01); *G01L 5/00* (2013.01)

(58) Field of Classification Search
CPC ........... G01N 29/4409; G01N 29/4427; G01N 29/4436; G01N 29/4445; G01N 29/4463; G01N 29/4472; G01N 29/48; G01L 1/2268; G01L 7/028; G01L 25/00; G01L 27/00; G01L 27/002; G01L 27/005; G01L 27/007; G06F 3/0418; G06F 8/658; G06F 2203/04105; G06F 3/0487
(Continued)

(56) References Cited

U.S. PATENT DOCUMENTS

2017/0110101 A1 4/2017 Cho et al.
2019/0114067 A1 4/2019 Xu et al.
(Continued)

FOREIGN PATENT DOCUMENTS

CN 103988433 8/2014
CN 105681562 6/2016
(Continued)

*Primary Examiner* — John Fitzgerald
*Assistant Examiner* — Truong D Phan
(74) *Attorney, Agent, or Firm* — Emerson, Thomson & Bennett, LLC; Roger D. Emerson; Matt J. Wilson

(57) ABSTRACT

Embodiments of the present disclosure provide a method and apparatus for determining a pressure reference value, and a chip and an electronic device. The method includes: consecutively acquiring N pressure signals by a pressure sensor; acquiring consecutive N pressure values on the basis of the N pressure signals; and determining a latest pressure reference value on the basis of the consecutive N pressure values and time characteristics of the consecutively acquired N pressure signals; wherein each of the pressure values is a difference between a sampling value corresponding to a pressure signal and the pressure reference value, and the consecutively acquired N pressure signals are acquired within a duration where a pressure is applied to the pressure sensor once, N being a positive integer greater than 0.

18 Claims, 6 Drawing Sheets

(58) Field of Classification Search
USPC ........................... 73/1.71, 1.57, 1.59; 702/98
See application file for complete search history.

(56) References Cited

U.S. PATENT DOCUMENTS

| | | | |
|---|---|---|---|
| 2019/0235649 | A1 | 8/2019 | Oyama et al. |
| 2020/0356216 | A1 | 11/2020 | Yamamoto et al. |

FOREIGN PATENT DOCUMENTS

| | | | | |
|---|---|---|---|---|
| CN | 110134295 | | | 8/2019 |
| CN | 110266876 | A | | 9/2019 |
| CN | 111630479 | | | 9/2020 |
| CN | 111797293 | | | 10/2020 |
| CN | 111797293 | A | * | 10/2020 |
| CN | 112099661 | | | 12/2020 |
| JP | 2019133239 | | | 8/2019 |

* cited by examiner

METHOD AND APPARATUS FOR DETERMINING PRESSURE REFERENCE VALUE, AND CHIP AND ELECTRONIC DEVICE

CROSS-REFERENCE TO RELATED APPLICATION

This disclosure is a continuation of international application No. PCT/CN2021/075406 filed on Feb. 5, 2021, which is hereby incorporated by reference in its entirety.

TECHNICAL FIELD

The present disclosure relates to the technical field of sensors, and in particular, relates to a method and apparatus for determining a pressure reference value, a chip, and an electronic device.

BACKGROUND

Human-computer interaction, as an important function of an electronic device, has been applied to various fields.

In the related art, human-computer interaction is based on a pressure detection solution. That is, a gesture operation of a user is identified by detecting a pressure value corresponding to a pressure signal acquired by a pressure sensor. The pressure value corresponding to the pressure signal refers to a differential between a sampling value of the pressure sensor and a sampling value of the pressure sensor in the case of a zero pressure (that is, no external pressure is applied to the pressure sensor). The sampling value of the pressure sensor in the case of the zero pressure is referred to as a pressure reference value. During performing gesture operations by the user, a pressure may be applied to the pressure sensor, and thus a pressure receiving surface of the pressure sensor is subjected to deformation from outside to inside. In this case, it is defined that positive pressure signals are present on the pressure receiving surface of the pressure sensor. In addition to the positive pressure signals present on the pressure receiving surface of the pressure sensor, invalid signals may also be present on the pressure receiving surface of the pressure sensor, for example, negative pressure signals. That is, the pressure receiving surface of the pressure sensor may be subjected to deformation from inside to outside. These invalid signals may cause some impacts to the pressure reference value, such that accuracy of pressure detection is lowered, and missed detection or false detection of user gesture operations is caused, thereby affecting user experience.

SUMMARY

Embodiments of the present disclosure provide a method and apparatus for determining a pressure reference value, and a chip and an electronic device, which are favorable to improving accuracy of pressure detection, and thus improving user experience.

In a first aspect, a method for determining a pressure reference value is provided. The method includes: consecutively acquiring N pressure signals by a pressure sensor; acquiring consecutive N pressure values on the basis of the N pressure signals; and determining a latest pressure reference value on the basis of the consecutive N pressure values and time characteristics of the consecutively acquired N pressure signals.

Generally, the pressure sensor may acquire pressure signals according to a fixed cycle, the acquired pressure signals are converted by an analog-to-digital converter to sampling values, pressure values are generated on the basis of differences from the sampling values and pressure reference values. That is, the acquired pressure values are also updated according to a fixed cycle, that is, one pressure value corresponds to one sampling value. However, the sampling values are not fixed even in the case that no external pressure is applied to the pressure sensor. For example, in the case that no external pressure is applied but external temperature is changed, the sampling value, the pressure reference value, and the pressure value may also be changed. Therefore, the pressure reference value also needs to be updated in real time, that is, one pressure value also corresponds to one pressure reference value.

On the basis of the latest pressure reference value, subsequent pressure values, for example, a first pressure value following the N pressure values, may be acquired.

A duration in which the pressure sensor is subjected to a pressure once may include any time period in an entire time period between the time when the pressure sensor is subjected to a positive pressure from outside to inside and the time when the pressure sensor is subjected to a negative pressure from inside to outside. For example, the duration in which the pressure sensor is subjected to the pressure once may include an entire time period between the time when a pressure receiving surface of the pressure sensor is in a deformation state from outside to inside and the time when the pressure receiving surface of the pressure sensor is in a deformation state from inside to outside. Still for example, the duration in which the pressure sensor is subjected to the pressure once may include only a time period in which the pressure receiving surface of the pressure sensor is in the deformation state from outside to inside, or the duration in which the pressure sensor is subjected to the pressure once may only include a time period in which the pressure receiving surface of the pressure sensor is in the deformation state from inside to outside.

By analyzing amplitude characteristics and time characteristics of the consecutively acquired N pressure signals, the latest pressure reference value is determined, such that it is favorable to acquisition of a relatively accurate pressure reference value to improve accuracy of pressure detection. In the case that the technical solution according to the embodiments of the present disclosure is applied to a human-computer interaction scenario, probability of missed detection or false detection of user gestures is lowered and user experience is enhanced.

In an optional embodiment, determining the latest pressure reference value on the basis of amplitudes of the consecutive N pressure values and the time characteristics of the consecutively acquired N pressure signals includes: identifying a magnitude relationship between an i-th pressure value and a first pressure threshold and/or a second pressure threshold; updating a positive pressure time $T\mathbf{1}_i$ according to $T\mathbf{1}_i = T\mathbf{1}_{i-1}$+predetermined time length in response to the i-th pressure value being greater than the first pressure threshold, wherein the positive pressure time $T\mathbf{1}_i$ is used to indicate a duration in which the pressure signal is at a positive pressure; determining a sampling value corresponding to the i-th pressure value as the latest pressure reference value in response to the positive pressure time $T\mathbf{1}_i$ being greater than a first time threshold, wherein the first pressure threshold is used to indicate whether the pressure sensor is subjected to the positive pressure from outside to inside, or updating a negative pressure time $T\mathbf{2}_i$ according to $T2_i = T2_{i-1}$+predetermined time length in response to the i-th pressure value being less than the second pressure threshold, wherein the negative pressure time $T2_i$ is used to indicate a duration in which the pressure signal is at a negative pressure; and determining a sampling value corresponding to the i-th pressure value as the latest pressure reference value in response to the negative pressure time $T2_i$ being greater than a second time threshold, wherein the second pressure threshold is used to indicate whether the pressure sensor is subjected to the negative pressure from inside to outside; wherein i is a positive integer greater than 0 and less than or equal to N.

By sequentially identifying the magnitude relationships between the N pressure values and the first pressure threshold and/or the second pressure threshold, it is identified that the pressure signals corresponding to the N pressure values are positive pressure signals or negative pressure signals, that is, the pressure signals are at a positive pressure or a negative pressure, and then it is further identified that the duration in which the pressure signals are at the positive pressure or the negative pressure. In the case that the duration in which the pressure signals are at the positive pressure is greater than the first time threshold or the duration in which the pressure signals are at the negative pressure being greater than the second time threshold, it may be considered that the pressure sensor is subjected to an abnormal press. In this case, the sampling value corresponding to a recently acquired pressure value is updated to the latest pressure reference value, such that the abnormal press does not affect accuracy of subsequent pressure detection.

In an optional embodiment, the method further includes: determining the pressure reference value as the latest pressure reference value in response to the positive pressure time $T1_i$ being less than or equal to the first time threshold; or determining the pressure reference value as the latest pressure reference value in response to the negative pressure time $T2_i$ being less than or equal to the second time threshold.

In the case that the duration in which the pressure signals are at the positive pressure being less than or equal to the first time threshold or the duration in which the pressure signals are at the negative pressure being less than or equal to the second time threshold, it may be considered that the pressure sensor is subjected to a normal press, and meanwhile, since the duration in which the pressure signals are at the positive pressure or the negative pressure is short, impacts caused by environmental factors to the pressure reference value may not be taken into consideration, that is, the pressure reference value is not updated. In this way, operation complexity may be lowered.

In an optional embodiment, the method further includes: identifying a magnitude relationship between an i-th pressure value and a first pressure threshold and a second pressure threshold; updating a no-pressure time $T3_i$ according to $T3_i = T3_{i-1}$+predetermined time length in response to the i-th pressure value being greater than or equal to the second pressure threshold and less than or equal to the first pressure threshold, wherein the no-pressure time $T3_i$ is used to indicate a duration in which the pressure sensor is subjected to no pressure; and determining a latest pressure reference value according to an infinite impulse response (IIR) filter function in response to the no-pressure time $T3_i$ being greater than a third time threshold, or determining the pressure reference value as a latest pressure reference value in response to the no-pressure time $T3_i$ being less than or equal to the third time threshold; wherein the first pressure threshold is used to indicate whether the pressure sensor is subjected to a positive pressure from outside to inside, and the second pressure threshold is used to indicate whether the pressure sensor is subjected to a negative pressure from inside to outside, i being a positive integer greater than 0 and less than or equal to N.

By sequentially identifying the magnitude relationship between the N pressure values and the first pressure threshold and/or the second pressure threshold, it is identified that the pressure signals corresponding to the N pressure values are subjected to no pressure, and the duration in which the pressure signals are at no pressure is further identified. In response to the duration in which the pressure signals are at no pressure being greater than the third time threshold, the pressure reference value may be updated by using the IIR filter function, to reduce the impacts caused by the environmental factors, such as temperature drift, to the pressure reference value. Likewise, in the case that the duration in which the pressure signals are at no pressure is less than or equal to the third time threshold, since the duration in which the pressure signals is at no pressure is short, the impacts caused the environmental factors to the pressure reference value may not be taken into consideration, that is, the pressure reference value is not updated. In this way, the operation complexity may be lowered.

In an optional embodiment, the filter function is $B_{i+1}=K*R+(1-K)*B_i$, wherein $B_{i+1}$ represents the latest pressure reference value, $B_i$ represents the pressure reference value corresponding to the i-th pressure value, K represents a filter coefficient in an IIR filter algorithm, and R represents the i-th pressure value.

In an optional embodiment, the predetermined time length is a sampling cycle for the pressure sensor.

In an optional embodiment, the first time threshold is in a range of 5 s to 10 s, and the second time threshold is less than or equal to the first time threshold.

In an optional embodiment, the first time threshold is in a range of 8 s to 10 s, and/or the second time threshold is 3 s.

In an optional embodiment, the third time threshold is 500 ms.

In an optional embodiment, an absolute value of the second pressure threshold is equal to an absolute value of the first pressure threshold.

The second pressure threshold is determined as a negative value of the first pressure threshold, which is simple and convenient in practice In an optional embodiment, the first pressure threshold is a pressure value corresponding to a weight of 150 g, and the second pressure threshold is a pressure value corresponding to a weight of −150 g.

In a second aspect, an apparatus for determining a pressure reference value. The apparatus includes: an acquiring unit, configured to consecutively acquire N pressure signals by a pressure sensor, and acquire consecutive N pressure values on the basis of the N pressure signals; and a determining unit, configured to determine a latest pressure reference value on the basis of the consecutive N pressure values and time characteristics of the consecutively acquired N pressure signals; wherein the pressure value is a difference between a sampling value corresponding to the pressure signal and the pressure reference value, and the consecutively acquired N pressure signals are acquired within a duration in which a pressure is applied to the pressure sensor once.

In an optional embodiment, the determining unit is specifically configured to: identify a magnitude relationship between an i-th pressure value and a first pressure threshold and/or a second pressure threshold; update a positive pressure time $T1_i$ according to $T1_i=T1_{i-1}$+predetermined time length in response to the i-th pressure value being greater than the first pressure threshold, wherein the positive pressure time $T1_i$ is used to indicate a duration in which the pressure signal is subjected to a positive pressure; and determine a sampling value corresponding to the i-th pressure value as the latest pressure reference value in response to the positive pressure time $T1_i$ being greater than a first time threshold, wherein the first pressure threshold is used to indicate whether the pressure sensor is subjected to the positive pressure from outside to inside, or update a negative pressure time $T2_i$ according to $T2_i=T2_{i-1}$+predetermined time length in response to the i-th pressure value being less than the second pressure threshold, wherein the negative pressure time $T2_i$ is used to indicate a duration in which the pressure signal is subjected to a negative pressure; and determine a sampling value corresponding to the i-th pressure value as the latest pressure reference value in response to the negative pressure time $T2_i$ being greater than a second time threshold, wherein the second pressure threshold is used to indicate whether the pressure sensor is subjected to the negative pressure from inside to outside; wherein i is a positive integer greater than 0 and less than or equal to N.

In an optional embodiment, the determining unit is further configured to determine the pressure reference value as the latest pressure reference value in response to the positive pressure time $T1_i$ being less than or equal to the first time threshold; or determine the pressure reference value as the latest pressure reference value in response to the negative pressure time $T2_i$ being less than or equal to the second time threshold.

In an optional embodiment, the determining unit is further configured to: identify a magnitude relationship between an i-th pressure value and a first pressure threshold and a second pressure threshold; update a no-pressure time $T3_i$ according to $T3_i=T3_{i-1}$+predetermined time length in response to the i-th pressure value being greater than or equal to the second pressure threshold and less than or equal to the first pressure threshold, wherein the no-pressure time $T3_i$ is used to indicate a duration in which the pressure sensor is subjected to no pressure; and determine a latest pressure reference value according to an IIR filter function in response to the no-pressure time $T3_i$ being greater than a third time threshold, or determine the pressure reference value as a latest pressure reference value in response to the no-pressure time $T3i$ being less than or equal to the third time threshold; wherein the first pressure threshold is used to indicate whether the pressure sensor is subjected to a positive pressure from outside to inside, and the second pressure threshold is used to indicate whether the pressure sensor is subjected to a negative pressure from inside to outside, i being a positive integer greater than 0 and less than or equal to N.

In an optional embodiment, the filter function is $B_{i+1}=K*R+(1-K)*B_i$, wherein $B_{i+1}$ represents the latest pressure reference value, $B_i$ represents the pressure reference value corresponding to the i-th pressure value, K represents a filter coefficient in an IIR filter algorithm, and R represents the i-th pressure value.

In an optional embodiment, the predetermined time length is a sampling cycle for the pressure sensor.

In an optional embodiment, the first time threshold is in a range of 5 s to 10 s, and the second time threshold is less than or equal to the first time threshold.

In an optional embodiment, the first time threshold is in a range of 8 s to 10 s, and/or the second time threshold is 3 s.

In an optional embodiment, the third time threshold is 500 ms.

In an optional embodiment, an absolute value of the first pressure threshold is equal to an absolute value of the second pressure threshold.

In an optional embodiment, the first pressure threshold is a pressure value corresponding to a weight of 150 g, and the second pressure threshold is a pressure value corresponding to a weight of −150 g.

In a third aspect, a device for determining a pressure reference value is provided. The device includes: a processor and a memory, wherein the memory is configured to store a computer program, and the processor, when calling and running the computer program stored in the memory, is caused to perform the method according to the first aspect or the various embodiments.

In a fourth aspect, a chip is provided. The chip includes: a processor, configured to, when calling and running a computer program from a memory, cause a device equipped with the chip to perform the method according to the first aspect or other optional embodiments.

In a fifth aspect, a computer-readable storage medium configured to store a computer program is provided, wherein the computer program, when run by a computer, causes the computer to perform the method according to the first aspect or other optional embodiments.

In a sixth aspect, an electronic device is provided. The electronic device includes the apparatus for determining the pressure reference value according to the second aspect and the various embodiments, and a pressure sensor.

DETAILED DESCRIPTION

The technical solutions according to the embodiments of the present disclosure are clearly and thoroughly described hereinafter with reference to the accompanying drawings illustrating the embodiments of the present disclosure.

Human-computer interaction, as an important function of an electronic device, has been applied to various fields.

The technical solutions according to the embodiments of the present disclosure are applicable to an electronic device equipped with a human-computer interaction interface. The electronic device may be, for example, a headset, a smart watch, a smart bracelet, or a mobile phone, and particularly, may be a headset. For example, the electronic device may be a true wireless stereo (TWS) headset. Since the headset is small, an operation surface of the headset is inevitably small, and the operation surface is coincident with a contact surface during wearing and thus mis-touches are caused, and blind operation is needed during wearing. Therefore, the human-computer interaction becomes particularly critical.

At present, in the related art, three mainstream human-computer interaction methods are available, that is, an acceleration sensor (G-sensor) solution, a capacitive touch solution, and a pressure detection scheme. In the acceleration sensor solution, the electronic device is provided with no physical key or touch pad, and operations on the electronic device only rely on an internal acceleration sensor thereof, and only a tap operation may be performed, but long-press and swipe operations may not be performed. In addition, tapping with a pressure may affect wearing comfort of the electronic device. In the capacitive touch solution, the electronic device generally includes three capacitive detection channels, and tap, long-press, swipe and the like operations or gestures may be performed, but mis-touches may frequently occur. In the pressure detection solution, a user operation is identified by detecting a pressure signal. As compared with the other two solutions, the pressure detection solution has merits of more types of gesture operations, and no mis-touches.

Figure 1:
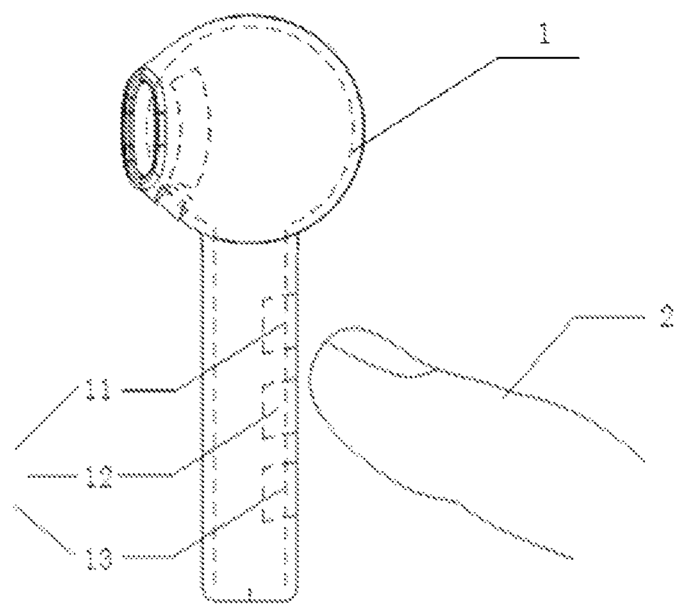
FIG. 1 is a schematic diagram of an application scenario according to some embodiments of the present application.

The embodiments of the present disclosure employ the pressure detection solution, such that an electronic device such as a mobile phone or a headset may be operated by a pressure applied by a user. Using a headset as an example, as illustrated in FIG. 1 which shows an electronic device 1 that is the headset, at least one pressure sensor is disposed on an earbud stem of the headset as the electronic device 1, for example, pressure sensors 11 to 13, the user may perform call, music control, volume adjustment, noise reduction mode switching and the like operations by single-tapping, double-tapping, long-pressing, swiping and the like gesture operations with a finger 2 of the user.

The pressure signals in the pressure detection solution are analog signals acquired by the pressure sensors, and are converted to digital signals by an analog-to-digital converter, that is, the sampling values according to the embodiments of the present disclosure. The pressure values are acquired by calculating difference between these sampling values and the pressure reference value. During performing gesture operations by the user, a pressure may be applied to the pressure sensor, and thus a pressure receiving surface of the pressure sensor is subjected to deformation from outside to inside. In this case, it is defined that positive pressure signals are present on the pressure receiving surface of the pressure sensor. In addition to the positive pressure signals present on the pressure receiving surface of the pressure sensor, invalid signals may also be present on the pressure receiving surface of the pressure sensor, for example, negative pressure signals. That is, the pressure receiving surface of the pressure sensor may be subjected to deformation from inside to outside. These invalid signals may cause some impacts to the pressure reference value, such that accuracy of pressure detection is lowered, and missed detection or false detection of user gestures is caused, thereby affecting user experience.

Various scenarios where impacts are caused to the pressure reference value according to some embodiments of the present disclosure are described hereinafter with reference to FIG. 2 to FIG. 7.

Figure 2:
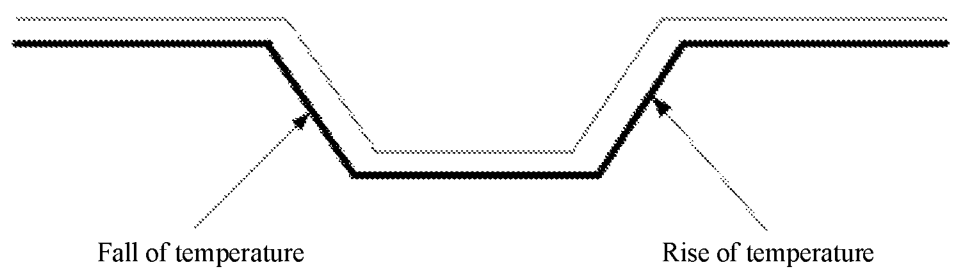
FIG. 2 to FIG. 7 illustrate various scenarios where impacts are caused to a pressure reference value according to some embodiments of the present disclosure.

Scenario 1: As illustrated in FIG. 2, in the case that the environmental temperature of the pressure sensor is changed, the sampling value of the pressure sensor subjected to a zero pressure may be drifted. As the temperature rises, the sampling value is up-shifted, and as the temperature falls, the sampling value is down-shifted. The speed of the drift is positively correlated with the changing speed of the temperature. That is, the more quickly the temperature is changed, the more quickly the sampling value is drifted; and the less quickly the temperature is changed, the less quickly the sampling value is drifted. In the case that the pressure reference value of the pressure sensor in this course remains unchanged, the pressure signal detected by the pressure sensor may be inaccurate, and mis-judgment by the electronic device where the pressure sensor is configured is caused. For example, where the environmental temperature rises to a specific value, a difference between the sampling value (that is, an actual pressure reference value of the pressure sensor) acquired by the pressure sensor subjected to the zero pressure and the pressure reference value stored on the electronic device may be mis-judged as a gesture operation of the user. Therefore, in this course, the pressure reference value needs to be changed with the environment.

Figure 3:
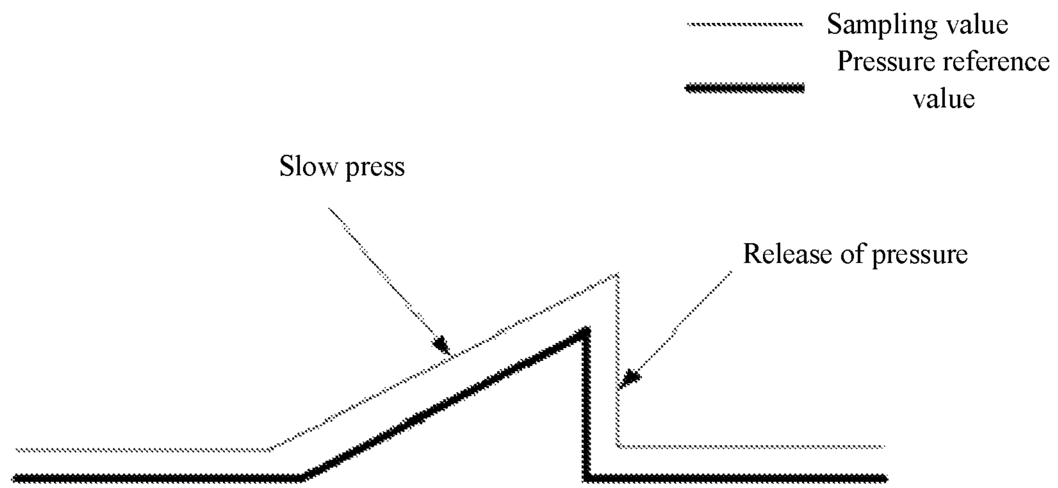

Scenario 2: As illustrated in FIG. 3, in the case that a pressure is being slowly applied to the pressure receiving surface of the pressure sensor, the sampling value acquired by the pressure sensor may slowly rise. Where the pressure is accumulated to a specific value, the pressure is abruptly released. In this case, the pressure signal acquired may be a positive pressure signal. Since slowly applying a pressure is considered as an abnormal user operation, where the pressure reference value in this course remains unchanged, likewise, the pressure signal detected by the pressure sensor may be inaccurate, and mis-judgment by the electronic device where the pressure sensor is configured is caused. For example, the course of slowly applying a pressure may be considered as a course where the temperature rises with respect to the pressure sensor. In the case that the pressure reference value is up-shifted in a fashion of processing the temperature drift, where the pressure is totally released, a difference between the sampling value acquired by the pressure sensor and the pressure reference value updated prior to release of the pressure corresponds to a negative pressure signal. This negative pressure signal may be specially processed by the electronic device. Therefore, the pressure reference value likewise needs to be updated in real time during this course.

Figure 4:
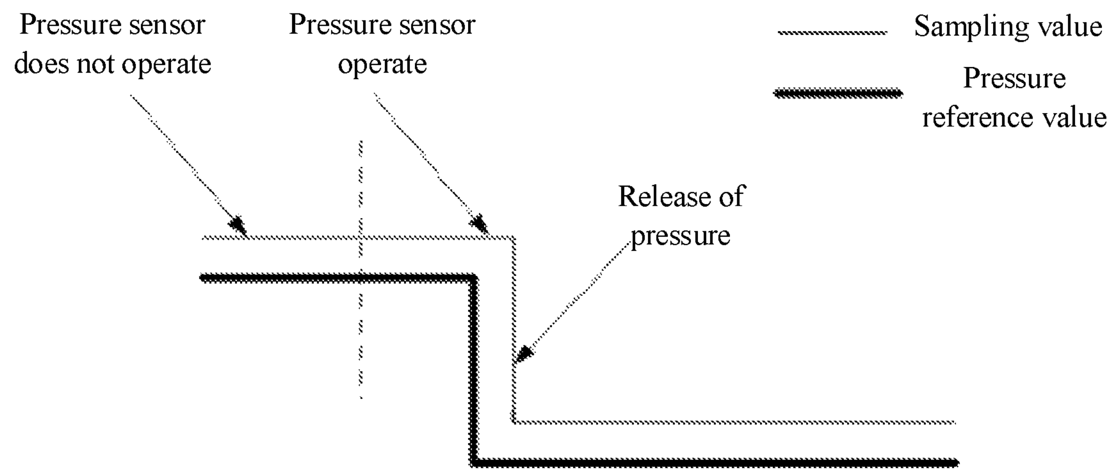

Scenario 3: As illustrated in FIG. 4, a pressure is applied to the pressure sensor before the pressure sensor operates, the pressure receiving surface of the pressure sensor may be subjected to deformation from outside to inside. Upon completion of the operation of the pressure sensor, the pressure is totally released, and in this case, the pressure value acquired may correspond to a negative pressure signal. Likewise, the press operation before the pressure sensor operates is considered as an abnormal user operation. For example, a first sampling value acquired upon start of the operation of the pressure sensor is taken as the pressure reference value, in the case that the pressure reference value remains unupdated upon release of the pressure, a difference between the sampling value acquired by the pressure sensor and the pressure reference value stored on the electronic device prior to release of the pressure may correspond to a negative pressure signal. The negative pressure signal may be specially processed by the electronic device. Therefore, the pressure reference value likewise needs to be updated in real time during this course.

Figure 5:
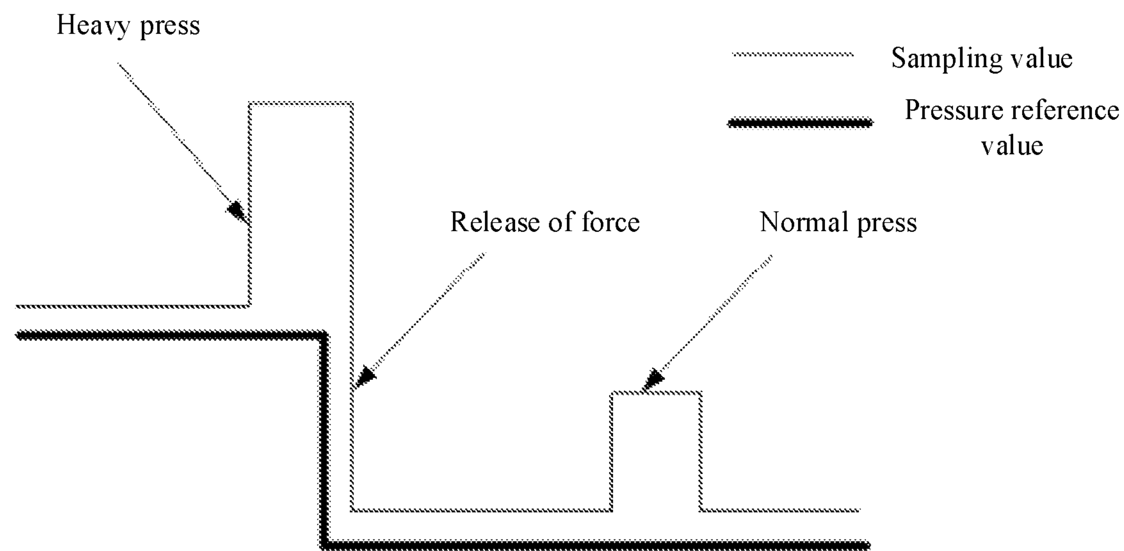

Scenario 4: As illustrated in FIG. 5, in the case that a greater pressure (that is, an abnormal press) is applied to the pressure receiving surface of the pressure sensor for a period of time, release of the pressure may cause the acquired pressure value to correspond to a negative pressure signal. That is, since the press is a heavy press, the pressure receiving surface of the pressure sensor takes a long time to restore to the original state. In the case that the pressure reference value is not updated upon release of the pressure, a difference between the sampling value acquired by the pressure sensor and the pressure reference value stored on the electronic device prior to release of the pressure may correspond to a negative pressure signal. The negative pressure signal may be specially processed by the electronic device. Therefore, the pressure reference value likewise needs to be updated in real time during this course.

Figure 6:
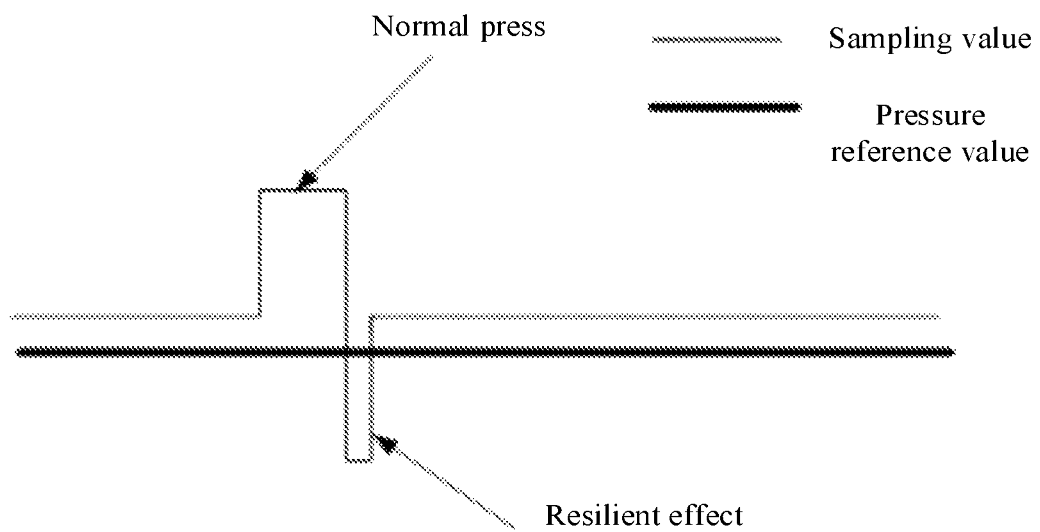

Scenario 5: As illustrated in FIG. 6, in the case that a normal pressure (that is, a normal press) is applied to the pressure receiving surface of the pressure sensor for a period of time, upon release of the pressure, under the effect of a resilient pressure, the pressure value acquired corresponds to a pulse negative pressure signal. Since the resilient pressure only lasts for a short period of time, the negative pressure signal also lasts for a short period of time. In this case, in the case that the pressure reference value is updated in real time, the pressure signal detected by the pressure sensor may be inaccurate, and mis-judgment by the electronic device where the pressure sensor is configured is caused. Therefore, the pressure reference value does not need to be updated in real time during this course.

Figure 7:
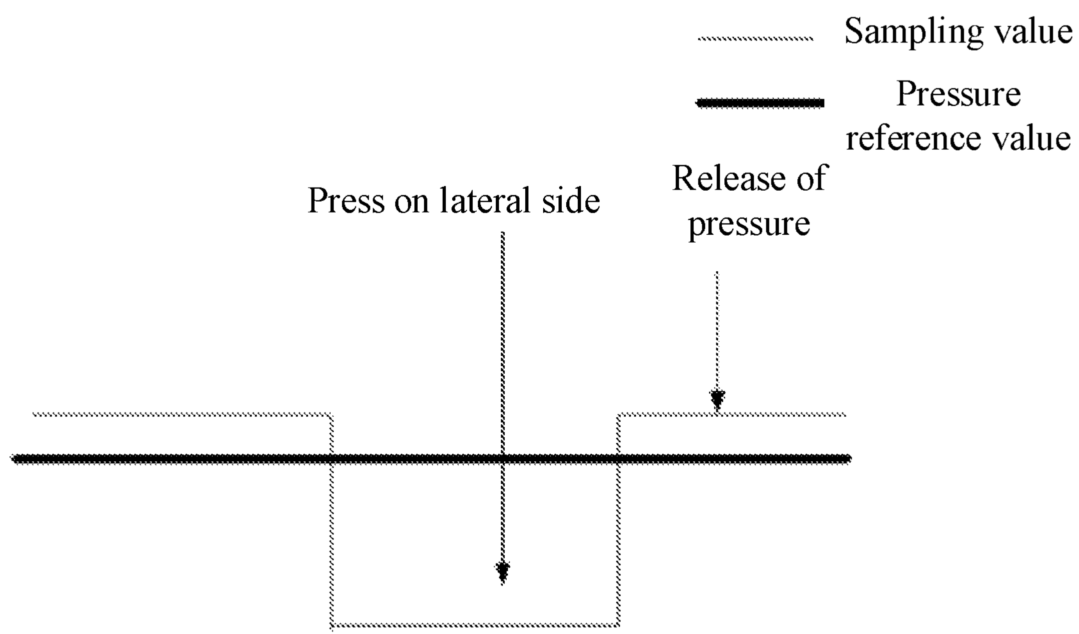

Scenario 6: As illustrated in FIG. 7, in the case that the user applies a pressure on a lateral side of the pressure sensor for a short period of time, due to the effect of pressure division, the pressure receiving surface of the pressure sensor may be subjected to deformation from inside to outside. In this case, the pressure value acquired corresponds to a negative pressure signal. Since it is impossible that the user not only applies a pressure on the lateral side of the pressure sensor but also applies a pressure on a front surface of the pressure sensor, the pressure reference value likewise does not need to be updated in real time during this course.

In consideration of various scenarios as described above, the embodiments of the present disclosure provide a method for determining a pressure reference value. In the method, a latest pressure reference value is determined by analyzing amplitude characteristics and time characteristics of pressure signals, such that an accurate pressure reference value is provided for subsequent pressure detection. In the case that the technical solution according to the embodiments of the present disclosure is applied to a human-computer interaction scenario, probability of missed detection or false detection of user gestures is lowered and user experience is enhanced.

Figure 8:
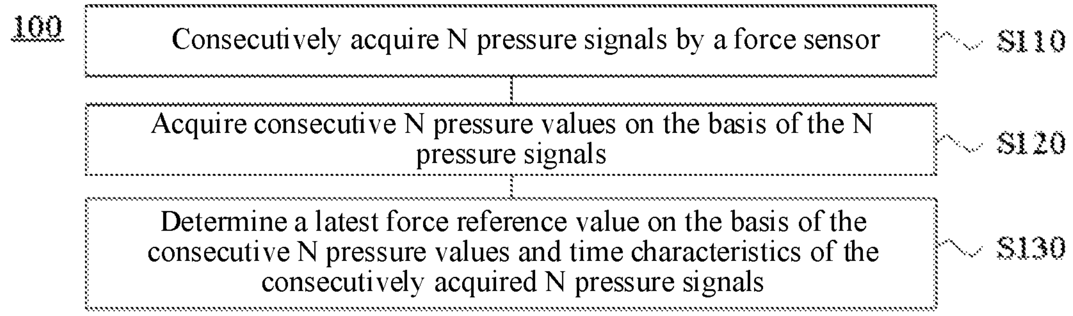
FIG. 8 is a schematic block diagram of a method for determining a pressure reference value according to some embodiments of the present disclosure.

FIG. 8 is a schematic block diagram of a method 100 for determining a pressure reference value according to some embodiments of the present disclosure. The method 100 may be performed by an electronic device, for example, the headset in FIG. 1, and particularly, may be performed by a processor of the electronic device. As illustrated in FIG. 8, the method 100 may include part or all of the following content.

In S110, the electronic device consecutively acquires N pressure signals by a pressure sensor.

In S120, the electronic device acquires consecutive N pressure values on the basis of the N pressure signals.

In S130, the electronic device determines a latest pressure reference value on the basis of the consecutive N pressure values and time characteristics of the consecutively acquired N pressure signals.

The pressure value is a difference between a sampling value corresponding to the pressure signal and the pressure reference value, and the consecutively acquired N pressure signals are acquired within a duration in which a pressure is applied to the pressure sensor, N being a positive integer greater than 0.

It should be noted that the method for determining the pressure reference value according to the embodiments of the present disclosure is not only applicable to headsets equipped with pressure sensors, but also applicable to other electronic devices equipped with pressure sensors. Although the description is given in this text using a headset as an example, the embodiments of the present disclosure are not limited to the headset.

In an embodiment of the present disclosure, the latest pressure reference value is employed to acquire a subsequent pressure value. It should be noted that the embodiments of the present disclosure do not limit the number of subsequent pressure values acquired using the latest pressure reference value. For example, the latest pressure reference value is employed to acquire the first pressure value following the N pressure values, or acquire M consecutive pressure values following the N pressure values.

In addition, it should be noted that the pressure reference value is a dynamic variable. That is, the electronic device generally stores only one pressure reference value, and in the case that the pressure reference value is changed, a previous pressure reference value is replaced by a latest pressure reference value.

Generally, the pressure sensor may acquire pressure signals according to a fixed cycle, the acquired pressure signals are converted by an analog-to-digital converter to sampling values, pressure values are generated on the basis of differences from the sampling values and pressure reference values. That is, the acquired pressure values are also updated according to a fixed cycle, that is, one pressure value corresponds to one sampling value. However, the sampling values are not fixed even in the case that no external pressure is applied to the pressure sensor. For example, in the case that no external pressure is applied but external temperature is changed, the sampling value, the pressure reference value, and the pressure value may also be changed. Therefore, the pressure reference value also needs to be updated in real time, that is, one pressure value also corresponds to one pressure reference value.

A duration in which the pressure sensor is subjected to a pressure once may include any time period in an entire time period between the time when the pressure sensor is subjected to a pressure from outside to inside and the time when the pressure sensor is subjected to a pressure from inside to outside. For example, the duration in which the pressure sensor is subjected to the pressure once may include an entire time period between the time when a pressure receiving surface of the pressure sensor is in a deformation state from outside to inside and the time when the pressure receiving surface of the pressure sensor is in a deformation state from inside to outside. Still for example, the duration in which the pressure sensor is subjected to the pressure once may include only a time period in which the pressure receiving surface of the pressure sensor is in the deformation state from outside to inside, or the duration in which the pressure sensor is subjected to the pressure once may only include a time period in which the pressure receiving surface of the pressure sensor is in the deformation state from inside to outside. For example, a single-tap operation on the headset by the user may be understood as a one-time pressure reception of the pressure sensor. However, in the case that the user double-taps the headset, since a time interval is present between two single-tap operations included in this double-tap operation, the double-tap operation does not belong to the one-time pressure reception.

It should be noted that the deformation from inside to outside of the pressure receiving surface of the pressure sensor may be caused by, for example, resilience induced by pressing pressures in scenario 2 to scenario 5, or induced by the lateral pressing pressure in scenario 6.

Optionally, in an embodiment of the present disclosure, the first pressure signal of the consecutively acquired N pressure signals may be a first pressure signal that the pressure from outside to inside is detected by the pressure sensor, or a first pressure signal that the pressure from inside to outside is detected by the pressure sensor.

Optionally, in the case that a pressure signal is acquired each time, a latest pressure reference signal is determined with the technical solution according to the embodiments of the present disclosure; or in the case that a plurality of pressure signals are consecutively acquired, a latest pressure reference value is determined with the technical solution according to the embodiments of the present disclosure. That is, although in the embodiments of the present disclosure, N pressure signals are consecutively acquired, a latest pressure reference value may be determined on the basis of pressure values corresponding to first i pressure signals and time characteristics of the first i pressure signals. The latest pressure reference value may be employed to acquire pressure values corresponding to pressure signals following the N pressure signals.

Optionally, in an embodiment of the present disclosure, determining the latest pressure reference value on the basis of amplitudes of the consecutive N pressure values and the time characteristics of the consecutively acquired N pressure signals includes: identifying a magnitude relationship between an i-th pressure value and a first pressure threshold and/or a second pressure threshold; updating a positive pressure time $T\mathbf{1}_i$ according to $T\mathbf{1}_i = T\mathbf{1}_{i-1}$+predetermined time length in response to the i-th pressure value being greater than the first pressure threshold, wherein the positive pressure time $T\mathbf{1}_i$ is used to indicate a duration in which the pressure signal is subjected to a positive pressure; determining a sampling value corresponding to the i-th pressure value as the latest pressure reference value in response to the positive pressure time $T\mathbf{1}_i$ being greater than a first time threshold, wherein the first pressure threshold is used to indicate whether the pressure sensor is subjected to the positive pressure from outside to inside, or updating a negative pressure time $T\mathbf{2}_i$ according to $T\mathbf{2}_i = T\mathbf{2}_{i-1}$+predetermined time length in response to the i-th pressure value being less than the second pressure threshold, wherein the negative pressure time $T\mathbf{2}_i$ is used to indicate a duration in which the pressure signal is subjected to a negative pressure; and determining a sampling value corresponding to the i-th pressure value as the latest pressure reference value in response to the negative pressure time $T\mathbf{2}_i$ being greater than a second time threshold, wherein the second pressure threshold is used to indicate whether the pressure sensor is subjected to the negative pressure from inside to outside; wherein i is a positive integer greater than 0 and less than or equal to N.

Optionally, in an embodiment of the present disclosure, the method further includes: determining the pressure reference value as the latest pressure reference value in response to the positive pressure time $T\mathbf{1}_i$ being less than or equal to the first time threshold; or determining the pressure reference value as the latest pressure reference value in response to the negative pressure time $T\mathbf{2}_i$ being less than or equal to the second time threshold.

In other words, the first time threshold is used to indicate that the duration in which the pressure sensor is subjected to the positive pressure is too long, that is, the pressure sensor is subjected to an abnormal press. Therefore, in response to the positive pressure time $T\mathbf{1}_i$ being less than or equal to the first time threshold, it is considered that the pressure sensor is in a normal state, and in this case, the pressure reference value does not need to be updated. On the contrary, in response to the positive pressure time $T\mathbf{1}_i$ being greater than the first time threshold, the pressure reference value needs to be updated in the above fashion. Likewise, the second time threshold is used to indicate that the duration in which the pressure sensor is subjected to the negative pressure is too long, that is, the pressure sensor has previously been subjected to an abnormal press. Therefore, in response to the negative pressure time $T\mathbf{2}_i$ being less than or equal to the second time threshold, it is considered that the pressure sensor is in a normal state, and in this case, the pressure reference value does not need to be updated. On the contrary, in response to the negative pressure time $T\mathbf{2}_i$ being greater than the second time threshold, the pressure reference value needs to be updated in the above fashion.

Optionally, in the case that N pressure values are acquired, magnitude relationships between the N pressure values and a predetermined pressure threshold 0 may be traversed. For example, magnitude relationships between a first pressure value to an N-th pressure value and a pressure threshold may be sequentially identified. In response to a pressure value being greater than 0, it may be considered that a pressure signal corresponding to the pressure value is at a positive pressure. In response to identifying that the first pressure value of the N pressure values is greater than 0, the positive pressure time starts being updated according to $T\mathbf{1}_i = T\mathbf{1}_{i-1}$+ predetermined time length. That is, the positive pressure time is defined as a variable $T\mathbf{1}$, and an initial value is defined as 0. In response to identifying that the first pressure value of the N pressure values is greater than 0, the positive pressure time is updated to $T\mathbf{1}_1$. In response to identifying that a second pressure value following the first pressure value is greater than 0, the positive pressure time is updated to $T\mathbf{1}_2$. Analogously, in response to identifying that an i-th pressure value following the previous pressure value greater than 0 is greater than 0, the positive pressure time is updated to $T\mathbf{1}_i$. In addition, each time a positive pressure time is updated, whether the positive pressure time is greater than a predetermined time threshold is identified, for example, the first time threshold in the embodiments of the present disclosure. In the case that the positive pressure time $T\mathbf{1}_i$ updated on the basis of the i-th pressure value is greater than the first time threshold, the sampling value corresponding to the i-th pressure value may be determined as the latest pressure reference value. That is, in the case that the positive pressure acts on the pressure sensor for a long period of time, the pressure may be considered as an abnormal press, and the pressure reference value is updated to the current sampling value to prevent the abnormal press from being mis-judged as a normal press. In this way, the situation where the electronic device mis-judges that a user gesture is made is avoided. Using the application scenario as illustrated in FIG. 3 as an example, since gesture interactions between the user and the electronic device are generally practiced by a brief press. In the case that the user slowly presses the pressure sensor and the slow press exceeds a specific period of time, it may be considered that the press is an abnormal press, and the pressure reference value needs to be updated. In the case that the positive pressure time $T1_i$ updated on the basis of the i-th pressure value is less than or equal to the first time threshold, the pressure reference value may not be updated. For example, the pressure reference value corresponding to the i-th pressure value may be determined as the latest pressure reference value.

Optionally, in the case that N pressure values are acquired, magnitude relationships between the N pressure values and a predetermined pressure threshold may be traversed. For example, magnitude relationships between a first pressure value to an N-th pressure value and a pressure threshold 0 may be sequentially identified. In response to a pressure value being less than 0, it may be considered that a pressure signal corresponding to the pressure value is at a negative pressure. In response to identifying that the first pressure value of the N pressure values is less than 0, the negative pressure time starts being updated according to $T2_i=T2_{i-1}+$ predetermined time length. That is, the negative pressure time is defined as a variable T2, and an initial value is defined as 0. In response to identifying that the first pressure value of the N pressure values is less than 0, the negative pressure time is updated to $T2_1$. In response to identifying that a second pressure value following the first pressure value is less than 0, the negative pressure time is updated to $T2_2$. Analogously, in response to identifying that an i-th pressure value following the previous pressure value less than 0 is less than 0, the positive pressure time is updated to $T2_i$. In addition, each time a negative pressure time is updated, whether the negative pressure time is greater than a predetermined time threshold is identified, for example, the second time threshold in the embodiments of the present disclosure. In the case that the negative pressure time $T2_i$ updated on the basis of the i-th pressure value is greater than the second time threshold, the sampling value corresponding to the i-th pressure value may be determined as the latest pressure reference value. That is, in the case that a negative pressure signal is present on the pressure sensor for a long period of time, it may be considered that the negative pressure signal needs to be canceled, for example, the negative pressure signal present in the application scenarios as illustrated in FIG. 3 to FIG. 5. In the case that the positive pressure time $T2_i$ updated on the basis of the i-th pressure value is less than or equal to the second time threshold, the pressure reference value may not be updated. For example, the pressure reference value corresponding to the i-th pressure value may be determined as the latest pressure reference value. Using the application scenario as illustrated in FIG. 6 as an example, since under the effect of a resilient pressure, a pulse negative pressure signal is acquired and the positive pressure signal lasts for a short period of time, the pressure reference value does not need to be updated. In this way, the situation where the pressure reference value restores to a negative pressure signal and hence a long-press event is generated by mistake upon release of the finger is avoided. With respect to the application scenario as illustrated in FIG. 7, since time and magnitude when the user presses the lateral side of the pressure sensor are generally approximate to time and magnitude when the user presses the front surface of the pressure sensor, that is, press time is generally less than a time threshold, under this scenario, in the case that the pressure sensor detects that a negative pressure signal is present, and a lasting time period of the negative pressure signal is less than a time threshold, the pressure reference value is not updated within the lasting time period. In this way, the situation where the pressure reference value restores to a negative pressure signal and hence a long-press event is generated by mistake upon release of the finger is avoided.

Optionally, two thresholds may be defined, a first pressure threshold and a second pressure threshold. The first pressure threshold may be greater than 0, and the second pressure threshold may be less than 0. In the case that a pressure value is greater than the first pressure threshold, it may be considered that a pressure signal corresponding to the pressure value is at a positive pressure. In the case that a pressure value is less than the second pressure threshold, it may be considered that a pressure signal corresponding to the pressure value is at a positive pressure.

Optionally, in the case that N pressure values are acquired, magnitude relationships between the N pressure values and a predetermined pressure threshold may be traversed. For example, magnitude relationships between a first pressure value to an N-th pressure value and a first pressure threshold and/or a second pressure threshold may be sequentially identified. In the case that a pressure value is greater than or equal to the second pressure threshold and less than or equal to the first pressure threshold, it may be considered that a pressure signal corresponding to the pressure value is at no pressure. In the case that that the first pressure value of the N pressure values is greater than or equal to the second pressure threshold and less than or equal to the first pressure threshold, the no-pressure time starts being updated according to $T3_i=T3_{i-1}+$predetermined time length. That is, the no-pressure time is defined as a variable T3, and an initial value is defined as 0. In response to identifying that the first pressure value of the N pressure values is greater than or equal to the first pressure threshold and less than or equal to the second pressure threshold, the no-pressure time is updated to $T3_1$. In the case that that a second pressure value following the first pressure value is greater than or equal to the first pressure threshold and less than or equal to the second pressure threshold, the no-pressure time is updated to $T3_2$. Analogously, in the case that that an i-th pressure value following the previous pressure value greater than or equal to the first pressure threshold and less than or equal to the second pressure threshold is greater than or equal to the first threshold and less than or equal to the second pressure threshold, the positive pressure time is updated to $T3_i$. In addition, each time a no-pressure time is updated, whether the no-pressure time is greater than a predetermined time threshold is identified, for example, the third time threshold in the embodiments of the present disclosure. In the case that the no-pressure time $T3_i$ updated on the basis of the i-th pressure value is greater than a third time threshold, the latest pressure reference value may be determined according to a filter function. In the case that the no-pressure time $T3_i$ updated on the basis of the i-th pressure value is less than or equal to the third time threshold, the pressure reference value may not be updated. For example, the pressure reference value corresponding to the i-th pressure value may be determined as the latest pressure reference value.

Specifically, the filter function is an IIR filter function, that is, $B_{i+1}=K*R+(1-K)*B_i$, wherein $B_{i+1}$ represents the latest pressure reference value, $B_i$ represents the pressure reference value corresponding to the i-th pressure value, K represents a filter coefficient in an IIR filter algorithm, and R represents a sampling value corresponding to the i-th pressure value.

For example, in the case that the electronic device where the pressure sensor is configured is just powered on, an initial pressure value detected by the pressure sensor is used as the pressure reference value. Generally, due to the impacts caused by the environmental factors such as temperature drift, the pressure reference value needs to be further processed to reduce the impacts caused to accuracy of the pressure signal. That is, in the case that the pressure sensor is successfully powered on, the pressure reference value needs to be updated in real time to reduce the impacts caused by the environmental factors such as temperature drift.

In practice, since a pressure signal generated by a gesture operation of the user is a high-frequency signal (which may be herein extended as including the positive pressure signal and the negative pressure signal according to the present disclosure). Signals generated by the temperature drift or other environmental factors are low-frequency signals. Therefore, a low-frequency component of a pressure value detected by the pressure sensor may be extracted in real time by the IIR filer algorithm as the pressure reference value.

It should be noted that the impacts caused by the environmental factors to the pressure reference value may also be processed by other filter fashions in addition to the IIR filtering, which is not limited in the embodiments of the present disclosure. For example, the latest pressure reference value may be determined only on the basis of a sampling value corresponding to the i-th pressure value and a pressure reference value corresponding to the i-th pressure value.

In an embodiment of the present disclosure, the filtering is not necessarily always needed. Whether the IIR filtering needs to be performed is determined according to a duration in which the pressure sensor is subjected to a pressure, such that operation complexity and power consumption are reduced while accuracy of the pressure reference value is ensured.

Optionally, updates of the positive pressure time, the negative pressure time, and the no-pressure time may all be practiced by a timer, specifically, by the following code.

```
If S>A1;
T1=T1+T;
T2=0;
T3=0;
Else
If S<A2;
T2=T2+T;
T1=0;
T3=0;
Else
T3=T2+T;
T1=0;
T2=0;
End
```

T represents the predetermined time length, which may be, for example, the sampling cycle for the pressure sensor; S is defined as the pressure value; A1 is defined as the first pressure threshold; A2 is defined as the second pressure threshold; T1 is defined as the positive pressure time; T2 is defined as the negative pressure time; and T3 is defined as the no-pressure time.

It should be noted that in the embodiments of the present disclosure, the fact that the signal is at no pressure means that no external pressure is applied to the pressure sensor, or an external pressure applied to the pressure sensor does not reach a specific value, for example, an external pressure caused by a mis-touch. Although the user applies a specific pressure, the magnitude of this pressure is small; and to prevent unnecessary mis-judgment induced by the mis-touch, the pressure sensor determines that the user applies a pressure only in response to determining that a detected pressure value reaches a specific value.

Optionally, in an embodiment of the present disclosure, the first time threshold may be in a range of 5 s to 10 s, specifically, in a range of 8 s to 10 s; and the second time threshold is less than or equal to the first time threshold, for example, 3 s.

Optionally, the third time threshold may be 500 ms.

Optionally, in an optional embodiment, an absolute value of the first pressure threshold may be equal to an absolute value of the second pressure threshold. For example, the first pressure threshold is a pressure value corresponding to a weight of 150 g, and the second pressure threshold is a pressure value corresponding to a weight of −150 g.

It should be noted that the above various values are only for illustrative purposes rather than causing any limitations to the technical solutions of the present disclosure. Various pressure signals may be relatively accurately identified on the basis of these values, and efficiency and power consumption of identification may also be improved. For example, a negative debounce generally lasts for a short period of time, and therefore, the second time threshold may be less than or equal to the first time threshold. In this way, accuracy, efficiency, and power consumption of the identification may be further improved.

In the case that the method according to the embodiments of the present disclosure is applied to an electronic device, the electronic device provides a human-computer interaction gesture interface for a user, and the electronic device is configured to identify, on the basis of a pressure signal, a gesture operation of the user on the interface.

Figure 9:
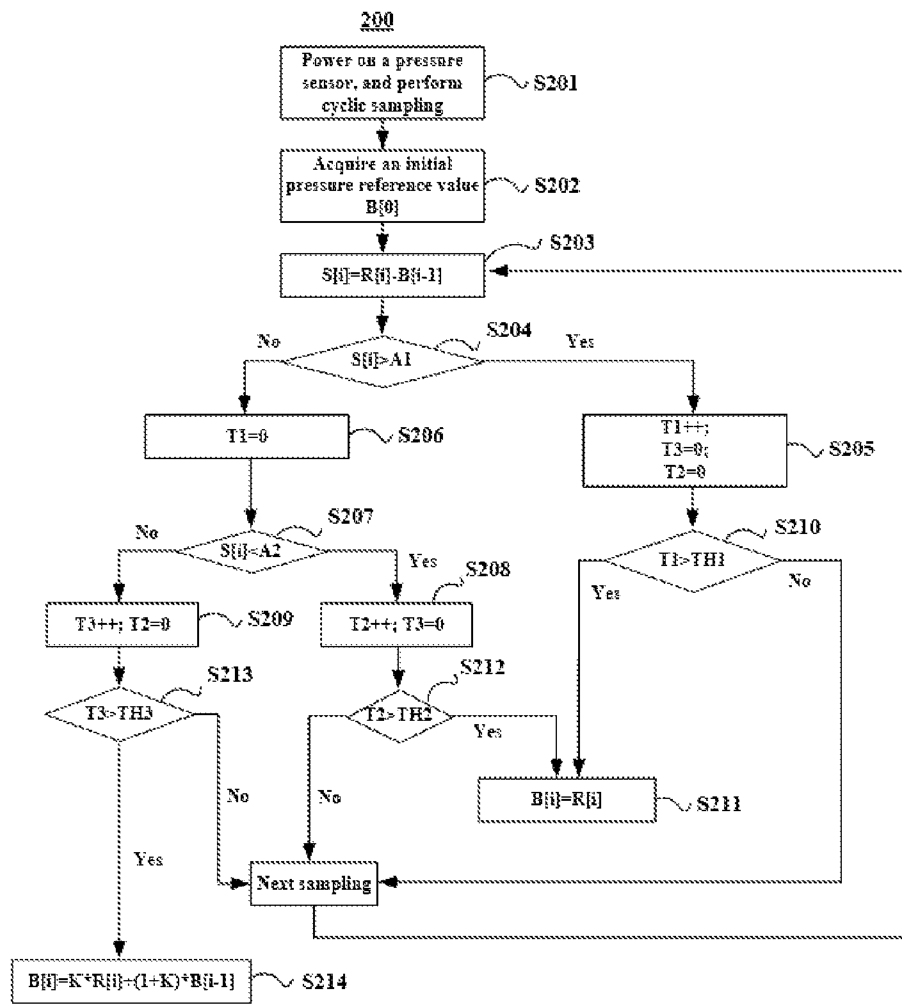
FIG. 9 is a schematic flowchart of the method for determining the pressure reference value according to some embodiments of the present disclosure.

A method 200 for determining a pressure reference value according to some embodiments of the present disclosure is described with reference to FIG. 9. As illustrated in FIG. 9, the method 200 includes the following content.

In S201, a pressure sensor is powered on, and cyclic sampling is performed.

In S202, an initial pressure reference value is acquired, and a first sampling value R[0] acquired by the pressure sensor is determined as an initial pressure reference value B[0].

In S203, a pressure value is determined on the basis of a difference between the sampling value and the pressure reference value, that is, S[i]=R[i]−B[i−1]. That is, the current pressure value is determined on the basis of a difference between the current sampling value and a previously determined pressure reference value, wherein i is a positive integer.

In S204, a magnitude relationship between S[i] and a threshold A1 (the first pressure threshold as described above) is identified. In the case that S[i] is greater than A1, the process proceeds to S205; and in the case that S[i] is less than or equal to A1, the process proceeds to S206.

In S205, a first timer T1 is controlled to start timing, a second timer T2 and a third timer T3 are reset, and the process proceeds to S210. The update of the positive pressure time is practiced by the second timer T2, and the update of the no-pressure time is practiced by the third timer T3.

In S206, the first timer T1 is reset, and the process proceeds to S207.

In S207, a magnitude relationship between S[i] and a threshold A2 (the first pressure threshold as described above) is identified. In the case that S[i] is less than A2, the process proceeds to S208; and in the case that S[i] is greater than or equal to A2, the process proceeds to S209.

In S208, the second timer T2 is controlled to start timing, the third timer T3 is reset, and the process proceeds to S212.

In S209, the third timer T3 is controlled to start timing, the second timer T2 is reset, and the process proceeds to S213.

In S210, whether a time length of the first timer T1 is greater than a first time threshold TH1. In the case that the time length of the first timer T1 is greater than the first time threshold TH1, the process proceeds to S211; and otherwise, the process proceeds to next sampling.

In S211, the pressure reference value is updated to the current sampling value, that is, B[i]=R[i].

In S212, whether a time length of the second timer T2 is greater than a second time threshold TH2. In the case that the time length of the second timer T2 is greater than the second time threshold TH2, the process proceeds to S211; and otherwise, the process proceeds to next sampling.

In S213, whether a time length of the third timer T3 is greater than a third time threshold TH3. In the case that the time length of the third timer T3 is greater than the third time threshold TH3, the process proceeds to S214; and otherwise, the process proceeds to next sampling.

In S214, the pressure reference value is updated according to B[i]−K*R[i]+(1−K)*B[i−1].

The method for determining the pressure reference value according to the embodiments of the present disclosure is described in detail hereinabove. Hereinafter, an apparatus for determining a pressure reference value according to some embodiments of the present disclosure is described with reference to FIG. 10. The technical feature described in the method embodiments may also apply to apparatus embodiments hereinafter.

Figure 10:
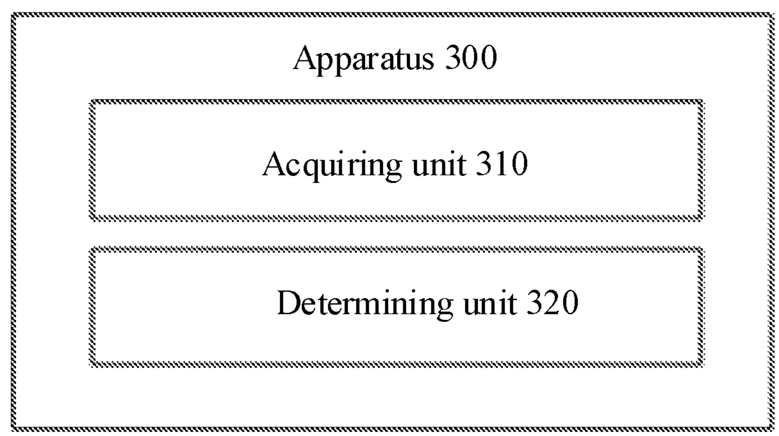
FIG. 10 is a schematic block diagram of an apparatus for determining a pressure reference value according to some embodiments of the present disclosure.

FIG. 10 is a schematic block diagram of an apparatus 300 for determining a pressure reference value according to an embodiment of the present disclosure. The apparatus 300 is applicable to an electronic device equipped with a pressure sensor. As illustrated in FIG. 10, the apparatus 300 includes:

an acquiring unit 310, configured to consecutively acquire N pressure signals by a pressure sensor, and acquire consecutive N pressure values on the basis of the N pressure signals; and a determining unit 320, configured to determine a latest pressure reference value on the basis of the consecutive N pressure values and time characteristics of the consecutively acquired N pressure signals; wherein each of the pressure value is a difference between a sampling value corresponding to a pressure signal and the pressure reference value, and the consecutively acquired N pressure signals are acquired within a duration in which a pressure is applied to the pressure sensor once.

Optionally, in an embodiment of the present disclosure, the determining unit 320 is specifically configured to:

identify a magnitude relationship between an i-th pressure value and a first pressure threshold and/or a second pressure threshold;

update a positive pressure time T1*i* according to T1*i*=T1*i*−1+predetermined time length in response to the i-th pressure value being greater than the first pressure threshold, wherein the positive pressure time T1*i* is used to indicate a duration in which the pressure signal is at a positive pressure; and determine a sampling value corresponding to the i-th pressure value as the latest pressure reference value in response to the positive pressure time T1*i* being greater than a first time threshold, wherein the first pressure threshold is used to indicate whether the pressure sensor is subjected to the positive pressure from outside to inside, or update a negative pressure time T2*i* according to T2*i*=T2*i*−1+predetermined time length in response to the i-th pressure value being less than the second pressure threshold, wherein the negative pressure time T2*i* is used to indicate a duration in which the pressure signal is at a negative pressure; and determine a sampling value corresponding to the i-th pressure value as the latest pressure reference value in response to the negative pressure time T2*i* being greater than a second time threshold, wherein the second pressure threshold is used to indicate whether the pressure sensor is subjected to the negative pressure from inside to outside;

wherein i is a positive integer greater than 0 and less than or equal to N.

Optionally, in an embodiment of the present disclosure, the determining unit 320 is further configured to:

determine the pressure reference value as the latest pressure reference value in response to the positive pressure time $T1_i$ being less than or equal to the first time threshold; or determining the pressure reference value as the latest pressure reference value in response to the negative pressure time T2*i* being less than or equal to the second time threshold.

Optionally, in an embodiment of the present disclosure, the determining unit 320 is further configured to:

identify a magnitude relationship between an i-th pressure value and a first pressure threshold and/or a second pressure threshold;

update a no-pressure time T3*i* according to T3*i*=T3*i*−1+predetermined time length in response to the i-th pressure value being greater than or equal to the second pressure threshold and less than or equal to the first pressure threshold, wherein the no-pressure time T3*i* is used to indicate a duration in which the pressure sensor is subjected to no pressure; and determine a latest pressure reference value according to a filter function in response to the no-pressure time T3*i* being greater than a third time threshold, or determine the pressure reference value as a latest pressure reference value in response to the no-pressure time T3*i* being less than or equal to the third time threshold;

wherein the first pressure threshold is used to indicate whether the pressure sensor is subjected to a positive pressure from outside to inside, and the second pressure threshold is used to indicate whether the pressure sensor is subjected to a negative pressure from inside to outside, i being a positive integer greater than 0, and i being less than or equal to N.

Optionally, in an embodiment of the present disclosure, the filter function is Bi+1=K*R+(1−K)*Bi, wherein Bi+1 represents the latest pressure reference value, Bi represents the pressure reference value, K represents a filter coefficient in an IIR filter algorithm, and R represents a sampling value corresponding to the i-th pressure value.

Optionally, in an embodiment of the present disclosure, the predetermined time length is a sampling cycle for the pressure sensor.

Optionally, in an embodiment of the present disclosure, the first time threshold is in a range of 5 s to 10 s, and the second time threshold is less than or equal to the first time threshold.

Optionally, in an embodiment of the present disclosure, the first time threshold is in a range of 8 s to 10 s, and/or the second time threshold is 3 s.

Optionally, in an embodiment of the present disclosure, the third time threshold is 500 ms.

Optionally, in an embodiment of the present disclosure, an absolute value of the first pressure threshold is equal to an absolute value of the second pressure threshold.

Optionally, in an embodiment of the present disclosure, the first pressure threshold is a pressure value corresponding to a weight of 150 g, and the second pressure threshold is a pressure value corresponding to a weight of −150 g.

Figure 11:
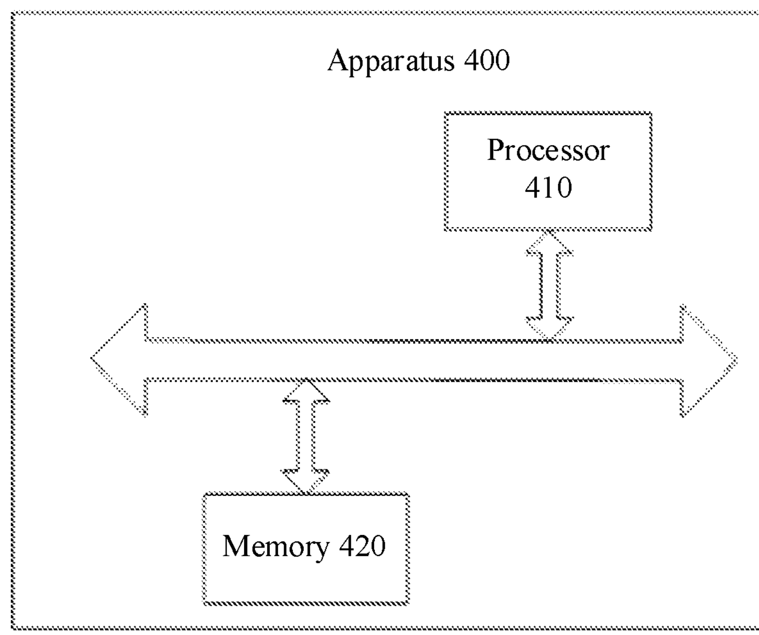
FIG. 11 is another schematic block diagram of the apparatus for determining the pressure reference value according to some embodiments of the present disclosure.

FIG. 11 is a schematic structural diagram of an apparatus 400 for determining a pressure reference value according to some embodiments of the present disclosure. The apparatus 400 for determining the pressure reference value as illustrated in FIG. 11 includes a processor 410. The processor 410 is capable of calling and running a computer program from a memory to perform the method according to the embodiments of the present disclosure.

Optionally, as illustrated in FIG. 9, the apparatus 400 for determining the pressure reference value includes a memory 420. The processor 410 is capable of calling and running a computer program from the memory 420 to perform the method according to the embodiments of the present disclosure.

The memory 420 may be a device independent of the processor 410, or may be integrated in the processor 410.

Optionally, the apparatus 400 for determining the pressure reference value may be specifically the apparatus 300 for determining the pressure reference value according to the embodiments of the present disclosure. The apparatus 400 for determining the pressure reference value is capable of performing the corresponding processes performed by the apparatus for updating the pressure reference value, which is not described hereinafter for brevity.

An embodiment of the present disclosure further provides a chip. The chip includes a processor. The processor is capable of calling and running a computer program from a memory to perform the method according to the embodiments of the present disclosure.

Optionally, the chip is applicable to the apparatus for determining the pressure reference value. The chip is capable of performing the corresponding processes performed by the apparatus for determining the pressure reference value, which is not described hereinafter for brevity.

It should be understood that the chip according to the embodiments of the present disclosure may also be referred to as a system-level chip, a system chip, a chip system, a system on chip, or the like.

Optionally, an embodiment of the present disclosure further provides a computer-readable storage medium. The computer-readable storage medium stores a computer program for performing the method according to the embodiments of the present disclosure.

A person skilled in the art may envisage that various exemplary units and algorithm steps described with reference to the embodiments of the present disclosure given herein may be practiced in the form of electronic hardware or a combination of computer software and electronic hardware. Whether such functions are implemented in the form of software or hardware depends on the specific application and the design restrictions applied to the entire system. Professional technical persons may implement the described functions by using different methods for each specific application. However, such implementation shall not be deemed as going beyond the scope of the present application.

A person skilled in the art would clearly acknowledge that for ease and brevity of description, the specific operation processes of the above described systems, apparatuses and units may be referenced to the relevant portions in the above described method embodiments, which are thus not described herein any further.

In the several embodiments provided in the present disclosure, it should be understood that the disclosed system, apparatus and method may be practiced in other manners. The above described apparatus embodiments are merely illustrative. For example, the unit division is merely logical function division and may be other divisions in actual practice. For example, a plurality of units or components may be combined or integrated into another device, or some features can be ignored or not performed. In addition, the displayed or discussed mutual couplings or direct couplings or communication connections may be implemented through some interfaces. The indirect couplings or communication connections between the apparatuses or units may be implemented in electronic, mechanical or other forms.

The units which are described as separate components may be physically separated or may be not physically separated, and the components which are illustrated as units may be or may not be physical units, that is, the components may be configured in the same position or may be distributed into a plurality of network units. Some of or all of the units may be selected according to actual needs to achieve the objectives of the solutions of the embodiments.

In addition, functional units in the embodiments of the present invention may be integrated into one processing unit, or each of the units may exist along physically, or two or more units may be integrated into one unit.

In the case that the functions are implemented in a form of a software functional unit and sold or used as an independent product, the units may be stored in a computer readable storage medium. On the basis of such an understanding, the technical solutions of the present disclosure essentially, or the part contributing to the related art, or all or a part of the technical solutions may be implemented in a form of a software product. The computer software product is stored in a storage medium and includes several instructions to cause a computer device (which may be a personal computer, a server, a network device, or the like) to perform all or some of steps of the methods described in the embodiments of the present disclosure. The storage medium includes various media capable of storing program code, for example, a USB flash disk, a removable hard disk, a read-only memory (ROM), a random-access memory (RAM), a magnetic disk, or an optical disc.

The above embodiments are used only for illustrating the present disclosure, but are not used to limit the protection scope of the present disclosure. Various modifications and replacements readily derived by those skilled in the art within technical disclosure of the present disclosure shall fall within the protection scope of the present disclosure. Therefore, the protection scope of the present disclosure is subject to the appended claims.

What is claimed is:

1. A method for determining a pressure reference value, comprising:

consecutively acquiring N pressure signals by a pressure sensor;

acquiring consecutive N pressure values on the basis of the N pressure signals; and determining a latest pressure reference value on the basis of the consecutive N pressure values and time characteristics of the consecutively acquired N pressure signals for replacing a current pressure reference value;

wherein each of the pressure values is a difference between a sampling value corresponding to a pressure signal and the current pressure reference value, and the consecutively acquired N pressure signals are acquired within a duration in which a pressure is applied to the pressure sensor once, N being a positive integer greater than 0, wherein determining the latest pressure reference value on the basis of the consecutive N pressure values and the time characteristics of the consecutively acquired N pressure signals for replacing the current pressure reference value comprises:

identifying a magnitude relationship between an i-th pressure value and a first pressure threshold and/or a second pressure threshold, wherein the first pressure threshold is used to indicate whether the pressure sensor is subjected to a positive pressure from outside to inside, and the second pressure threshold is used to indicate whether the pressure sensor is subjected to a negative pressure from inside to outside; and updating a positive pressure time $T\mathbf{1}_i$ according to $T\mathbf{1}_i=T\mathbf{1}_{i-1}$+predetermined time length in response to the i-th pressure value being greater than the first pressure threshold, wherein the positive pressure time $T\mathbf{1}_i$ is used to indicate a duration in which the pressure signal is at a positive pressure; and determining a sampling value corresponding to the i-th pressure value as the latest pressure reference value in response to the positive pressure time $T\mathbf{1}_i$ being greater than a first time threshold for replacing the current pressure reference value, or updating a negative pressure time $T\mathbf{2}_i$ according to $T\mathbf{2}_i=T\mathbf{2}_{i-1}$+predetermined time length in response to the i-th pressure value being less than the second pressure threshold, wherein the negative pressure time $T\mathbf{2}_i$ is used to indicate a duration in which the pressure signal is at a negative pressure; and determining a sampling value corresponding to the i-th pressure value as the latest pressure reference value in response to the negative pressure time $T\mathbf{2}_i$ being greater than a second time threshold for replacing the current pressure reference value;

wherein i is a positive integer greater than 0 and less than or equal to N.

2. The method according to claim 1, further comprising:

determining the current pressure reference value as the latest pressure reference value in response to the positive pressure time $T\mathbf{1}_i$ being less than or equal to the first time threshold; or determining the current pressure reference value as the latest pressure reference value in response to the negative pressure time $T\mathbf{2}_i$ being less than or equal to the second time threshold.

3. The method according to claim 1, further comprising:

updating a no-pressure time $T\mathbf{3}_i$ according to $T\mathbf{3}_i=T\mathbf{3}_{i-1}+$ predetermined time length in response to the i-th pressure value being greater than or equal to the second pressure threshold and less than or equal to the first pressure threshold, wherein the no-pressure time $T\mathbf{3}_i$ is used to indicate a duration in which the pressure sensor is subjected to no pressure; and determining the latest pressure reference value according to a filter function in response to the no-pressure time $T\mathbf{3}_i$ being greater than a third time threshold for replacing the current pressure reference value, or determining the current pressure reference value as the latest pressure reference value in response to the no-pressure time $T\mathbf{3}_i$ being less than or equal to the third time threshold.

4. The method according to claim 3, wherein the filter function is $B_{i+1}=K*R+(1-K)*B_i$, wherein $B_{i+1}$ represents the latest pressure reference value, $B_i$ represents the pressure reference value, K represents a filter coefficient in an infinite impulse response IIR filter algorithm, and R represents the i-th pressure value.

5. The method according to claim 1, wherein the predetermined time length is a sampling cycle for the pressure sensor.

6. The method according to claim 1, wherein the first time threshold is in a range of 5 s to 10 s, and the second time threshold is less than or equal to the first time threshold.

7. The method according to claim 6, wherein the first time threshold is in a range of 8 s to 10 s, and/or the second time threshold is 3 s.

8. The method according to claim 7, wherein the first pressure threshold is a pressure value corresponding to a weight of 150 g, and the second pressure threshold is a pressure value corresponding to a weight of −150 g.

9. A chip, comprising a processor configured to call and execute a computer program from a memory to perform the method according to claim 1.

10. An apparatus for determining a pressure reference value, applicable to an electronic device equipped with a pressure sensor, comprising:

a processor and a memory, wherein the memory is configured to store a computer program, and the processor is configured to, when calling and running the computer program stored in the memory, perform operations of:

consecutively acquiring N pressure signals by the pressure sensor, and acquiring consecutive N pressure values on the basis of the N pressure signals; and determining a latest pressure reference value on the basis of the consecutive N pressure values and time characteristics of the consecutively acquired N pressure signals for replacing a current pressure reference value;

wherein each of the pressure values is a difference between a sampling value corresponding to a pressure signal and the current pressure reference value, and the consecutively acquired N pressure signals are acquired within a duration in which a pressure is applied to the pressure sensor once, N being a positive integer greater than 0 wherein determining the latest pressure reference value on the basis of the consecutive N pressure values and the time characteristics of the consecutively acquired N pressure signals for replacing the current pressure reference value comprises:

identifying a magnitude relationship between an i-th pressure value and a first pressure threshold and/or a second pressure threshold, wherein the first pressure threshold is used to indicate whether the pressure sensor is subjected to a positive pressure from outside to inside, and the second pressure threshold is used to indicate whether the pressure sensor is subjected to a negative pressure from inside to outside; and updating a positive pressure time $T\mathbf{1}_i$ according to $T\mathbf{1}_i=T_{i-1}$+predetermined time length in response to the i-th pressure value being greater than the first pressure threshold, wherein the positive pressure time $T\mathbf{1}_i$ is used to indicate a duration in which the pressure signal is at a positive pressure; and determining a sampling value corresponding to the i-th pressure value as the latest pressure reference value in response to the positive pressure time $T1_i$ being greater than a first time threshold for replacing the current pressure reference value, or updating a negative pressure time $T2_i$ according to $T2_i=T2_{i-1}$+predetermined time length in response to the i-th pressure value being less than the second pressure threshold, wherein the negative pressure time $T2_i$ is used to indicate a duration in which the pressure signal is at a negative pressure; and determining a sampling value corresponding to the i-th pressure value as the latest pressure reference value in response to the negative pressure time $T2_i$ being greater than a second time threshold for replacing the current pressure reference value;

wherein i is a positive integer greater than 0 and less than or equal to N.

11. The apparatus according to claim 10, wherein the processor is further configured to, when calling and running the computer program stored in the memory, perform operations of:

determining the current pressure reference value as the latest pressure reference value in response to the positive pressure time $T1_i$ being less than or equal to the first time threshold; or determining the current pressure reference value as the latest pressure reference value in response to the negative pressure time $T2_i$ being less than or equal to the second time threshold.

12. The apparatus according to claim 10, wherein the processor is further configured to, when calling and running the computer program stored in the memory, perform operations of:

updating a no-pressure time $T3_i$ according to $T3_i=T3_{i-1}$+ predetermined time length in response to the i-th pressure value being greater than or equal to the second pressure threshold and less than or equal to the first pressure threshold, wherein the no-pressure time $T3_i$ is used to indicate a duration in which the pressure sensor is subjected to no pressure; and determining the latest pressure reference value according to a filter function in response to the no-pressure time $T3_i$ being greater than a third time threshold for replacing the current pressure reference value, or determining the current pressure reference value as the latest pressure reference value in response to the no-pressure time $T3_i$ being less than or equal to the third time threshold.

13. The apparatus according to claim 12, wherein the filter function is $B_{i+1}=K*R+(1-K)*B_i$, wherein Bin represents the latest pressure reference value, $B_i$ represents the pressure reference value corresponding to the i-th pressure value, K represents a filter coefficient in an infinite impulse response IIR filter algorithm, and R represents the i-th pressure value.

14. The apparatus according to claim 10, wherein the predetermined time length is a sampling cycle for the pressure sensor.

15. The apparatus according to claim 10, wherein the first time threshold is in a range of 5 s to 10 s, and/or the second time threshold is less than or equal to the first time threshold.

16. The apparatus according to claim 15, wherein the first time threshold is in a range of 8 s to 10 s, and/or the second time threshold is 3 s.

17. The apparatus according to claim 16, wherein the first pressure threshold is a pressure value corresponding to a weight of 150 g, and the second pressure threshold is a pressure value corresponding to a weight of −150 g.

18. An electronic device, comprising a pressure sensor and an apparatus, wherein the electronic device provides a human-computer interaction gesture interface for a user, and the electronic device is configured to identify, based on a pressure signal, a gesture operation of the user on the interface, the apparatus comprises: a processor configured to call and run a program unit from a memory; to perform operations of:

consecutively acquiring N pressure signals by a pressure sensor, and acquiring consecutive N pressure values on the basis of the N pressure signals; and determining a latest pressure reference value on the basis of the consecutive N pressure values and time characteristics of the consecutively acquired N pressure signals for replacing a current pressure reference value;

wherein each of the pressure values is a difference between a sampling value corresponding to a pressure signal and the current pressure reference value, and the consecutively acquired N pressure signals are acquired within a duration in which a pressure is applied to the pressure sensor once, N being a positive integer greater than 0, wherein determining the latest pressure reference value on the basis of the consecutive N pressure values and the time characteristics of the consecutively acquired N pressure signals for replacing the current pressure reference value comprises:

identifying a magnitude relationship between an i-th pressure value and a first pressure threshold and/or a second pressure threshold, wherein the first pressure threshold is used to indicate whether the pressure sensor is subjected to a positive pressure from outside to inside, and the second pressure threshold is used to indicate whether the pressure sensor is subjected to a negative pressure from inside to outside; and updating a positive pressure time $T1_i$ according to $T1_i=T1_{i-1}$+predetermined time length in response to the i-th pressure value being greater than the first pressure threshold, wherein the positive pressure time $T1_i$ is used to indicate a duration in which the pressure signal is at a positive pressure; and determining a sampling value corresponding to the i-th pressure value as the latest pressure reference value in response to the positive pressure time $T1_i$ being greater than a first time threshold for replacing the current pressure reference value, or updating a negative pressure time $T2_i$ according to $T2_i=T2_{i-1}$+predetermined time length in response to the i-th pressure value being less than the second pressure threshold, wherein the negative pressure time $T2_i$ is used to indicate a duration in which the pressure signal is at a negative pressure; and determining a sampling value corresponding to the i-th pressure value as the latest pressure reference value in response to the negative pressure time $T2_i$ being greater than a second time threshold for replacing the current pressure reference value;

wherein i is a positive integer greater than 0 and less than or equal to N.

* * * * *